(12) United States Patent
Kawanabe

(10) Patent No.: US 7,139,368 B2
(45) Date of Patent: Nov. 21, 2006

(54) X-RAY CT APPARATUS

(75) Inventor: Shinya Kawanabe, Nasushiobara (JP)

(73) Assignees: Kabushiki Kaisha Toshiba, Tokyo (JP); Toshiba Medical Systems Corporation, Otawara (JP)

(*) Notice: Subject to any disclaimer, the term of this patent is extended or adjusted under 35 U.S.C. 154(b) by 0 days.

(21) Appl. No.: 11/271,849

(22) Filed: Nov. 14, 2005

(65) Prior Publication Data

US 2006/0104412 A1 May 18, 2006

(30) Foreign Application Priority Data

Nov. 15, 2004 (JP) .............................. 2004-329967

(51) Int. Cl.
*H05G 1/28* (2006.01)
*H05G 1/60* (2006.01)

(52) U.S. Cl. ........................... 378/162; 378/165; 378/4

(58) Field of Classification Search ..................... 378/4, 378/15, 19–27, 162, 165

See application file for complete search history.

(56) References Cited

U.S. PATENT DOCUMENTS

2003/0123603 A1* 7/2003 Suzuki .......................... 378/4

FOREIGN PATENT DOCUMENTS

JP 2000-116634 4/2000

* cited by examiner

*Primary Examiner*—Courtney Thomas
*Assistant Examiner*—Irakli Kiknadze
(74) *Attorney, Agent, or Firm*—Oblon, Spivak, McClelland, Maier & Neustadt, P.C.

(57) ABSTRACT

An X-ray CT apparatus has an operating guide unit for guiding a series of operations necessary from preparation till completion of scanning. The operating guide unit selectively displays a patient information input operating guide, a scanogram imaging operating guide, a scan plan selection operating guide, a scan range setting operating guide, a bed move starting guide, a scan operating guide, and a scan completion operating guide, in accordance with respective operation stages.

16 Claims, 17 Drawing Sheets

| Operating stage | Operating guide |
|---|---|
| [Guided Mode] Button is pressed | "Operating : Start" |
| Five seconds offer displaying "operating guide : start" | "Operating : Patient entry" |
| Patient ID and name are input | "Operating : Scan condition selection" |
| Scano mode is selected | "Operating : S&S, SS&V, Dynamic Scan" |
| S&V mode is selected | "Operating : S&S, SS&V, Dynamic Scan" |
| Dynamic Scan mode is selected | "Operating : S&S, SS&V, Dynamic Scan" |
| Helical Scan mode is selected | "Operating : Helical Scan" |
| Scan planning | "Operating : Scan planning" |
| [Confirm] Button is pressed in Scan planning | "Operating : Bed moving" |
| after start position inputting | "Operating : Bed moving" |
| Scanning is completed | "Operating : Scan completed" |
| [Quit eXam] Button is pressed | "Operating : Examination is completed" |
| [Next Patient] Button is pressed | Guide is over |

FIG. 3

Patient ID: 1234567890
Patient name: TEST
Age:   Sex:
First contrast medium:
Second contrast medium:
Second contrast medium:

1234567890
TEST

WL: 0 WW: 1000

○△ button | ○× button
×□ button | ×♪ button
△○ button | △♪ button

Mask

Mask

| No. | Elm. Start | Start time | Pause time | Start position | End position | Scan mode | Scan No. | KV | mA | Scan speed (Total seconds) |
|---|---|---|---|---|---|---|---|---|---|---|
| 1 | >P | *** | *** | | | Scano | 90D | 120 | 150 | |
| 2 | >P | | 0.0 | | | Helcal | 1 | 120 | 250 | 0.75(18.0) |

Operating guide : scanogram (1) Move preliminarily.
When start button flickers, press start button.

(2) Start scanogram imaging.
When start button lights up, press start button.

(3) When interrupt button is pressed, imaging is interrupted.

[Cancel]

Copy | New scan | Delete | Additional scan | Confirm
Reserve | Patient information | Irradiation

Operating guide : imaging condition select (1) Select site of inspection (head, chest, etc.) from human figure shown on left.

(2) Select imaging condition.

[Cancel]

Patient ID:
Patient name: Alphabet or katakana : (family name) space (first name)
Date of birth: yyyy.mm.dd  Age:
Sex:  Body weight:     kg
Patient comment:
First contrast medium:
Second contrast medium:
Site of inspection:

Cancel  Detail

Emergency

Mask

○ Easy Mode Head-1    2 SU/HU
○ Easy Mode Head-2    3 SU/HU

Guided mode

Reserve | Patient information | Irradiation

○× button | ○△ button
×♪ button | ×□ button
△ button | △○ button

Patient ID: 1234567890
Patient name: TEST
Age:   Sex:
First contrast medium:
Second contrast medium:
Second contrast medium:

Mask

Mask

| ○△ button | ○× button |
| --- | --- |
| × □ button | × ♪ button |
| △ ○ button | △ ♪ button |

Operating guide : S&S, S&V, dynamic scan (1) Start imaging
When start button lights up, press start button.

(2) When interrupt button is pressed, imaging is interrupted.

[Cancel]

| No. | Elm. Start | Start time | Pause time | Start position | End position | Scan mode | Scan No. | KV | mA | Scan speed (Total seconds) |
| --- | --- | --- | --- | --- | --- | --- | --- | --- | --- | --- |
| 1 > P | | *** | 0.0 | | | S&V | 15 | 120 | 200 | 0.75(11.25) |

Copy | New scan | Delete | Additional scan | Confirm

Reserve | Patient information | Irradiation

X-RAY CT APPARATUS

CROSS-REFERENCE TO RELATED APPLICATIONS

This application is based upon and claims the benefit of priority from prior Japanese Patent Application No. 2004-329967, filed Nov. 15, 2004, the entire contents of which are incorporated herein by reference.

BACKGROUND OF THE INVENTION

1. Field of the Invention

The present invention relates to an X-ray CT apparatus (X-ray computed tomographic apparatus) for reconstructing images of the inside of a subject.

2. Description of the Related Art

There is an X-ray CT apparatus which reconstructs images of the inside of a subject by emitting X-rays to the subject from multiple directions, and handling the X-rays having passed through the subject as projection data.

To acquire and reconstruct the images of the inside of the subject by the X-ray CT apparatus, various settings are required, including: scan conditions such as tube voltage and tube current of an X-ray tube and X-ray emission time; a scanning method such as dynamic scan and helical scan; and a scanning range.

Accordingly, in a recent X-ray CT apparatus, scan operations are divided into small operation states, including: storage of information given to images to be scanned, such as a subject ID and a subject name; review of a scanning range by scanogram scanning; setting of scan conditions to determine scan conditions by dividing the scanning zone into small positions such as head, chest and abdomen; scan planning for minutely specifying the scanning ranges; bed moving for moving a bed to the scanning start position; and a scan operation for scanning as desired. An operator of the apparatus sets the operations at each stage of operation, completes the operation stage by stage, and finally acquires the desired images of the inside of the subject (see, for example, Jpn. Pat. Appln. KOKAI Publication No. 2003-204960).

As a result, it is not required to set all the conditions at a time to scan in the subject, and demand for professional knowledge of scanning of the operator of the apparatus is considerably alleviated.

However, an operating method peculiar to an X-ray CT apparatus used still demands professional knowledge and skill. Along with continued development of the X-ray CT apparatus and rapid progress in the medical technique, specifications of the X-ray CT apparatus are changing, and operating methods are also changing. Besides, operating methods vary depending on manufacturers and types of X-ray CT apparatuses.

Therefore, an operator of the apparatus not experienced sufficiently in a specific X-ray CT apparatus must set the conditions at each stage of operation of the X-ray CT apparatus while referring to an operation manual and checking an operating screen of the apparatus, and prompt inspection may not be always expected.

BRIEF SUMMARY OF THE INVENTION

It is an object of the invention to improve controllability of an X-ray CT apparatus.

According to an aspect of the present invention, there is provided an X-ray CT apparatus comprising: a gantry having an X-ray tube and an X-ray detector in order to scan a subject; an operating guide unit to guide a series of operations at least necessary from preparation till completion of the scanning; a controlling unit which controls the gantry in accordance with the operation; and a reconstructing unit which reconstructs image data on the basis of data collected by the scanning, wherein, in accordance with the operation stages, the operating guide unit selectively displays: a patient information input operating guide to urge input of a patient identification number and a patient name; a scanogram imaging operating guide to urge instruction of start of preliminary move of a bed for scanogram imaging, and instruction of start of scanogram imaging; a scan plan selection operating guide to urge selection of a scanning position and selection of a scan plan; a scan range setting operating guide to urge setting of a scan range on the scanogram; a bed move starting guide to urge instruction of start of move of the bed to the scan start position; a scan operating guide to urge instruction of start of the scan and to confirm scan interrupt operation; and a scan completion operating guide to confirm continuation of the scan and to urge instruction of completion of the scan.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 shows a table held by the guide unit of the embodiment;

FIG. 9 is a view of a display screen showing an operating guide at a stage of scan condition selection operation in the embodiment;

FIG. 10 is a view of a display screen showing an operating guide at a stage of scanogram operation in the embodiment;

FIG. 12 is a view of a display screen showing an operating guide at a stage of bed moving operation in the embodiment;

FIG. 13 is a view of a display screen showing an operating guide at a stage of S&S, S&V or dynamic scan operation in the embodiment;

FIG. 14 is a view of a display screen showing an operating guide at a stage of helical scan operation in the embodiment;

FIG. 15 is a view of a display screen showing an operating guide at a stage of scan completion operation in the embodiment.

DETAILED DESCRIPTION OF THE INVENTION

Figure 1:
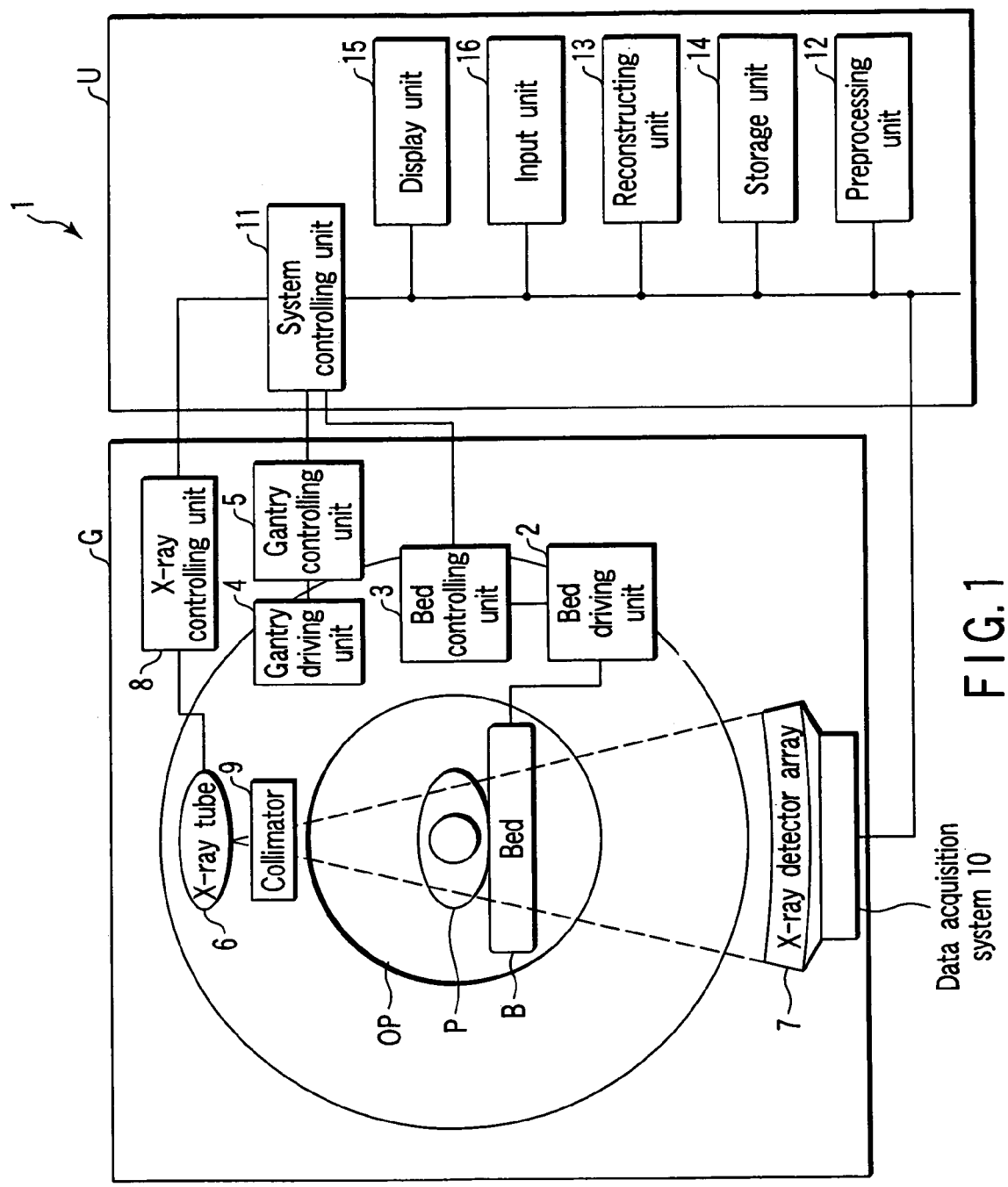
FIG. 1 is a block diagram showing a configuration of an X-ray CT apparatus according to an embodiment.
Figure 2:
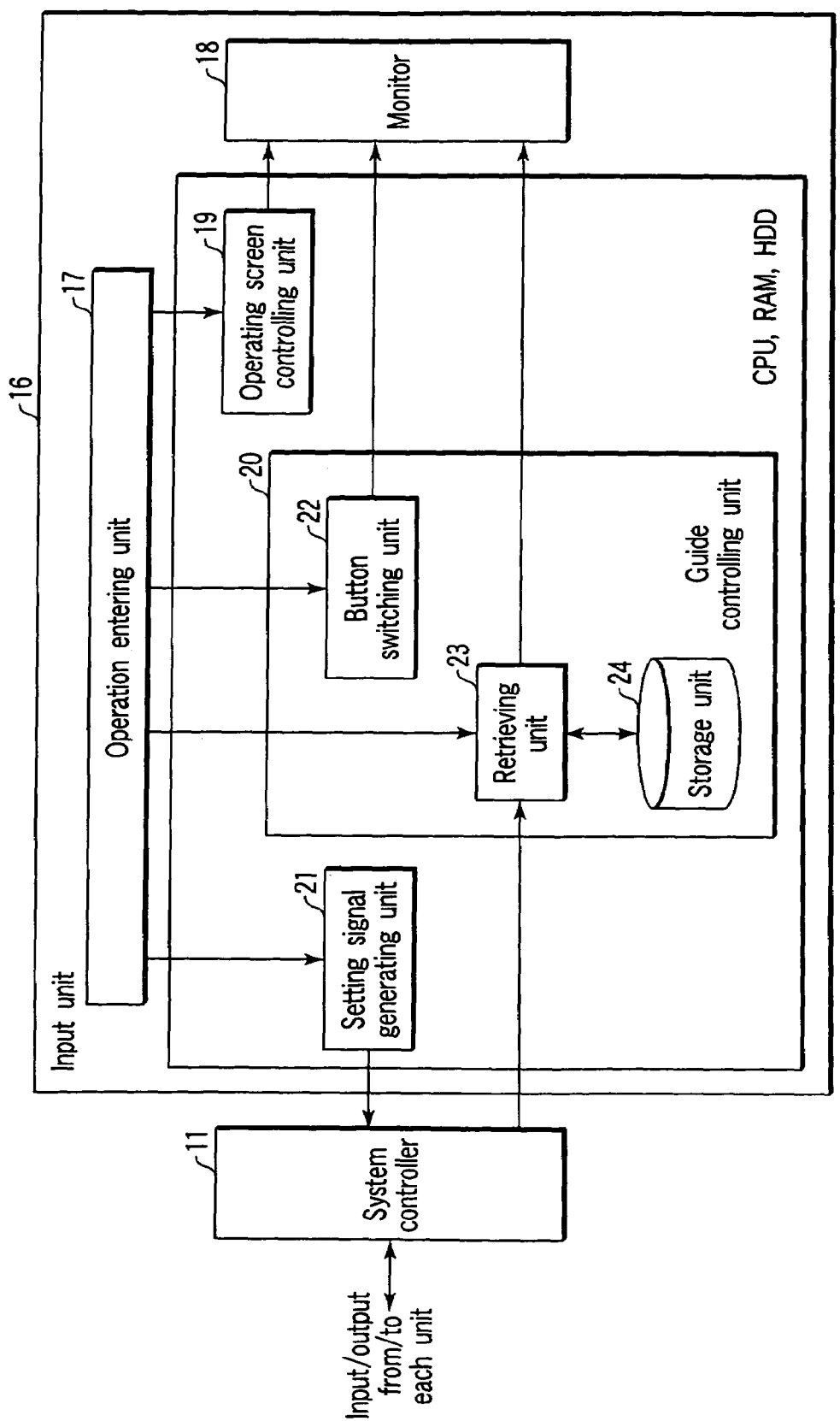
FIG. 2 is a detailed block diagram of a guide unit included in the X-ray CT apparatus according to the embodiment.
Figure 4A:
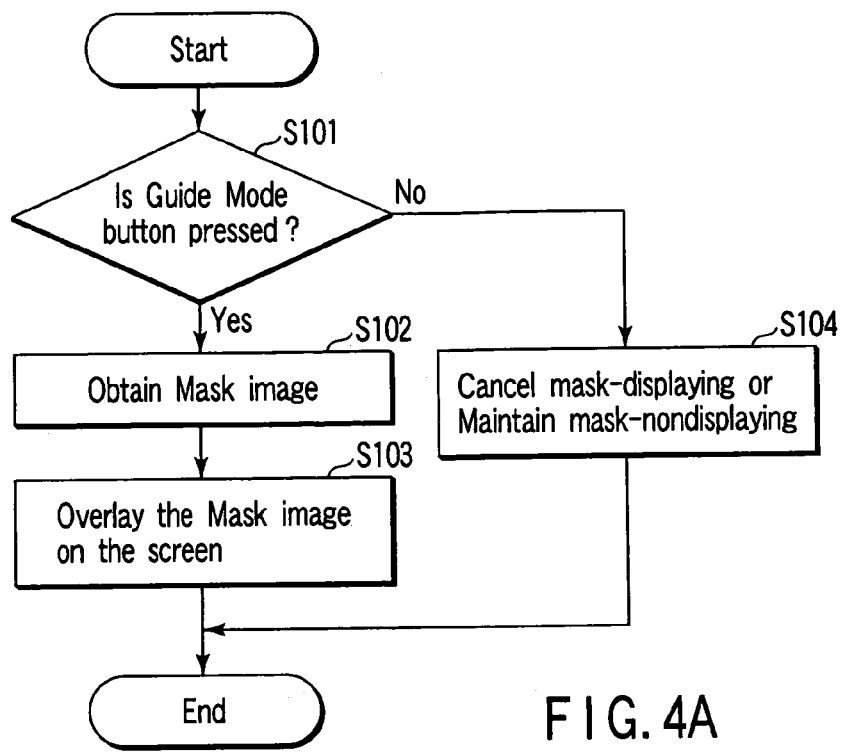
FIG. 4A is a flowchart explaining an operation of masking a predetermined position on an operating screen in the embodiment.

An embodiment of the present invention will be described below in detail with reference to FIGS. 1 to 16. FIG. 1 is a block diagram showing a configuration of an X-ray CT apparatus according to the embodiment of the invention. FIG. 2 is a detailed block diagram of a guide unit included in the X-ray CT apparatus according to the embodiment. FIG. 3 shows a table held by the guide unit of the embodiment. FIG. 4 is a flowchart explaining an operation of masking a predetermined position on an operating screen. FIG. 5 is a flowchart explaining an operation of displaying an operating guide. FIGS. 6 to 16 are views showing operating guides displayed at various stages of operation of the X-ray CT apparatus according to the embodiment.

The X-ray CT apparatus 1 shown in FIG. 1 is an apparatus for reconstructing the inside of a subject as images, by emitting X-rays to the subject while varying a position of the subject to which the X-rays are emitted, and projecting reversely the inside of the subject on the basis of the transmitted X-rays. It is intended to obtain the images of the inside of the subject finally by scanning operations including stages of operation for executing scanogram scanning, various scans, and scan planning.

In an inputting device 16 specifically shown in FIG. 2, necessary inputs are entered at each stage of scanning operation of the X-ray CT apparatus 1. Corresponding to each stage of operation, operating guides as shown in FIGS. 6 to 16 are displayed to guide an operator of the apparatus into correct input operation, and other than an input button and an input field essential for the present scanning operation is concealed by a mask.

The configuration of the X-ray CT apparatus 1 will be more specifically described below. As shown in FIG. 1, the X-ray CT apparatus 1 comprises: a gantry G having an opening OP; a bed B which mounts a subject P and is placed into the opening OP; and a processing unit U for controlling the entire gantry G and bed B in dialogue with the operator of the apparatus, collecting projection data, and reconstructing images.

The bed B is a top panel for mounting the subject, and includes a bed driving unit 2 and a bed controlling unit 3. The bed B is driven by the bed driving unit 2 to slide in the longitudinal direction, and is placed into the opening OP. The bed driving unit 2 is controlled by the bed controlling unit 3 to determine the driving timing and driving amount. Control by the bed controlling unit 3 corresponds to a bed control signal outputted from the processing unit U. The bed controlling unit 3 returns an operation completion signal to the processing unit U when operation is completed at each stage of operation.

The gantry G includes a gantry driving unit 4 and a gantry controlling unit 5, and revolves about the center of axis in the opening direction of the opening OP by means of the gantry driving unit 4. The gantry driving unit 4 is controlled by the gantry controlling unit 5 to determine the driving timing and driving amount. Control by the gantry controlling unit 5 corresponds to a gantry control signal outputted from the processing unit U. The gantry controlling unit 5 returns an operation completion signal to the processing unit U when operation is completed at each stage of operation.

Inside of the gantry G, an X-ray tube 6 and an X-ray detecting array 7 are disposed. In addition, an X-ray controlling unit 8 and a collimator 9 corresponding to the X-ray tube 6, and a data acquisition system 10 corresponding to the X-ray detecting array 7 are similarly disposed inside of the gantry G. The X-ray tube 6 and X-ray detecting array 7 are disposed at opposite positions on both sides of the opening OP.

The X-ray tube 6 emits an X-ray toward the subject. The X-ray emitted from the X-ray tube 6 is a cone beam X-ray or fan beam X-ray whose exposure range is limited in the subject body width direction and body axis direction by means of the collimator 9 installed in the neighborhood. The X-ray tube 6 emits X-rays at the tube voltage, tube current and exposure time controlled by the X-ray controlling unit 8. The X-ray controlling unit 8 controls the X-ray tube corresponding to an X-ray control signal outputted from the processing unit U. The X-ray emitted by this mechanism passes through the subject, and the transmitted X-ray is detected by the X-ray detecting array 7.

The X-ray detecting array 7 is a two-dimensional X-ray detector having a plurality X-ray detecting elements composed of scintillators and photo diodes disposed in an array configuration in two directions orthogonal to each other. The shape is an arc centered on the focus of X-ray generated by the X-ray tube. The X-ray detected by the X-ray detecting array is converted into a detection signal by each X-ray detecting element, and collected in the data acquisition system 10. The data acquisition system 10 outputs the collected detection signals to the processing unit U. Collection timing by the data acquisition system 10 is controlled by a timing control signal outputted from the processing unit U. The detection signal outputted contains an integral value of each absorption coefficient along the transmission length of X-rays sequentially passing through substances different in X-ray absorption coefficient, and is used as projection data of the inside of the subject.

The processing unit U includes a system controlling unit 11 for outputting control signals to the bed controlling unit 3, gantry controlling unit 5, X-ray controlling unit 8, and data acquisition system 10, and receiving operation completion signals. It also includes a preprocessing unit 12, a reconstructing unit 13, a storing unit 14, and a displaying unit 15 as devices for processing the detection signals outputted from the data acquisition system 10, and forming images.

The preprocessing unit 12 corrects sensitivity and X-ray intensity of projection data composed of detection signals, and the reconstructing unit 13 reversely projects the corrected projection data mainly by using reconstruction algorithm called Feldkamp method, and reconstructs the inside of the subject as image data. The reconstructed image data is stored in the storing unit 14 together with the subject ID and name. The displaying unit 15 is composed of, for example, a monitor and a scan converter. The reconstructed image data is read out from the storing unit by the scan converter, and converted into a format conforming to the monitor, and the reconstructed inside of the subject is displayed in the monitor as images.

The control signal outputted from the system controlling unit 11 corresponds to each stage of operation of the X-ray CT apparatus 1. That is, the X-ray CT apparatus 1, until displaying the images of the inside of the subject, operates in sequential stages, including: an operation stage of giving attributes to an image, such as a subject ID or subject name; an operation stage of scanogram; an operation stage of setting scan conditions to determine a position to be scanned, such as head or abdomen; an operation stage of scan planning; and various scan operation stages. Depending on the operation stages, control signals are generated on the basis of the input by the operator of the apparatus, and outputted to a predetermined controlling unit.

The X-ray CT apparatus 1 transfers to each operation stage through dialogue with the operator of the apparatus, and finally scans the desired range in the inside of the subject by a desired scanning method, and acquires the images of the inside of the subject as images having desired attributes. The processing unit U includes the inputting unit 16 for exchanging dialogue with the operator of the apparatus. The system controlling unit 11 sequentially sends out control signals and operation completion signals to the inputting unit 16 to keep dialogue with the operator of the apparatus.

That is, in the X-ray CT apparatus 1, first of all, the operator of the apparatus enters the subject ID and subject name. Next, the operator of the apparatus enters for scanogram scanning. When scanogram scanning is over, the operator enters which position is inspected, such as head, chest or abdomen of the subject, in other words, which position is scanned. Further, the operator sets the scan conditions by entering the flow from scanning to image acquisition, a scanning method, reconstructing conditions, and displaying and recording conditions. After setting of scan conditions, scan planning is entered to determine which range out of the selected position is scanned. After input of scan planning, a command is entered to start moving of the bed to the entered scanning range. After moving the bed, input according to each scanning method is entered. When scanning is over, whether to scan again or not is entered, and whether to terminate inspection or not is entered. This series of inputs is entered depending on each operation stage by using the inputting unit 16. Therefore, the inputting unit 16 is a man-machine interface for the X-ray CT apparatus 1 demanding setting and selection by the operator of the apparatus in order to perform an operation desired by the operator of the apparatus.

The inputting unit 16 is composed of, as shown in FIG. 2, computer resources such as a CPU, a RAM, a ROM, an HDD and others (not shown), an operation entering unit 17 including a touch panel, a mouse, a keyboard and others, and a monitor 18 having a display screen. The ROM or HDD includes an application for causing the inputting unit 16 to function as a man-machine interface with respect to the X-ray CT apparatus 1. On the basis of the application, the CPU performs arithmetic operations, and the RAM stores the results of operations, whereby the inputting unit 16 further includes, aside from the operating entering unit 17, an operating screen controlling unit 19, a guide controlling unit 20, and a setting signal generating unit 21.

The operating screen controlling unit 19 holds an operating screen including button images and input fields for accepting setting inputs by the operator of the apparatus at each stage of operation of the X-ray CT apparatus 1 as image data. The operating screen controlling unit 19 receives control signals and operation completion signals outputted from the system controlling unit 11, and also receives input signals from the operation entering unit 17. These signals are interpreted, an operating screen for transferring the X-ray CT apparatus 1 to the next operation stage is sent out to the monitor 18, and operating screens as shown in FIGS. 6 to 16 are displayed on the display screen.

The setting signal generating unit 21 interprets the input signal outputted when the operation entering unit accepts the operation of the operator of the apparatus, and generates a setting signal corresponding to each operation stage. The setting signal is generated and outputted to the system controlling unit 11, and the X-ray CT apparatus 1 is controlled on the basis of the setting signal. The inputs using the operation entering unit 17 are those entered by pressing the button images on the operating screen show in FIGS. 6 to 16 displayed on the monitor 18 by the operating screen controlling unit 19, and inputs into input fields, and setting signals are generated by interpreting such pressing or inputs.

The guide controlling unit 20 includes a button switching unit 22, a retrieving unit 23, and a storing unit 24. The guide controlling unit 20 is a unit of guiding the operation of the X-ray CT apparatus 1 in accordance with each operation stage.

The button switching unit 22 of the guide controlling unit 20 switches between display and non-display of buttons for setting details on the operating screen. Specifically, when an inexperienced operator of the apparatus attempts to make a series of operations, unnecessary buttons are concealed by masking, such as buttons for functioning unnecessary sub-functions or buttons for setting details of input fields or the like. Masking includes non-display of detail setting buttons for limiting specific functions, and rejection of operations on detail setting buttons.

In accordance with operation stages, the guide controlling unit 20 selectively displays: a patient identification input operating guide for urging input of a patient identification number and patient name; a scanogram imaging operating guide for instructing start of preliminary move of a bed for scanogram imaging and urging instruction to start scanogram imaging; a scan plan selection operating guide for urging selection of a scanning position and urging selection of a scan plan; a scan range setting operating guide for urging setting of a scan range on scanogram; a bed move starting guide for urging to instruct start of move of the bed to a scan start position; a scan operating guide for urging instruction of scan start, and confirming a scan interrupt operation; and a scan completion operating guide for urging confirmation of continued scan and instruction of completion of scan.

The button switching unit 22 starts to operate when receiving the input signal from the operation entering unit 17 corresponding to pressing of a guide button on the operating screen. The mask is held by the button switching unit 22, and when the guide button is pressed, this mask is fetched, and overlaid and displayed in a predetermined position. The predetermined position is on the button for detail setting.

In the button switching unit 22, the case where switching of display and non-display of the buttons for detail setting is performed by overlaying of the mask is explained in this embodiment. However, the button for detail setting on the screen may be concealed by other means. In this case, the button switching unit 22 controls the operating screen controlling unit 19. The button switching unit 22 receives an input signal, and instructs the image data to be displayed in the operating screen controlling unit 19.

The button for detail setting includes, for example, a reference position setting button, a respiration control button, a sound batch OFF button, an auto film button, an auto sort button, a status button, a patient comment input field, and a scan condition change tag, etc.

The reference position setting button is a button for setting the scan start position at a set value (0 mm, etc.). The respiration control button is a button for setting to insert sound automatically before and after scan depending on the scan time. The sound batch OFF button is a button for turning off all sound set by respiration control or the like. The auto film button is a button for setting filming of images of the inside of the subject reconstructed in cooperation with various scans automatically. The auto sort button is a button for setting to automatically shuffle images of the inside of the subject reconstructed in cooperation with various scans. The status button is a button for setting to acquire a status of an electrocardiograph. The scan condition change tag includes tags of continuous scan, reconstruction parameter, expanding function, and window condition, and the tag is for setting and entering the scan range, reconstruction function, etc.

The storing unit 24 stores operating guides. Operating guides are prepared in correspondence with respective operation stages, and show image data for guiding input by the operator of the apparatus necessary for executing the respective operation stages. Also as shown in FIG. 3, the storing unit 24 stores a correspondence table in which operation stages and operating guides are corresponded to each other. Actually, the operation corresponds to the signal inputted in the guide controlling unit 20. The corresponding signal is a control signal, an operation completion signal, an input waiting signal, or an input signal by the operator of the apparatus accepted in the operation entering unit 17. That is, an operating guide for urging input necessary at the next operation stage, and an operating guide for urging input necessary for executing an operation desired by the operator of the apparatus are stored in correspondence with the triggering signals.

The retrieving unit 23 retrieves the operating guide corresponding to each operation stage, outputs to the monitor 18, and displays the retrieved operating guide on the display screen. The retrieving unit 23 receives the control signal, operation completion signal, or input waiting signal outputted by the system controlling unit 11, or the input signal based on the input accepted in the operation entering unit. Using the received signal as a retrieval key, the retrieving unit 23 searches whether or not an operation stage conforming to the retrieval key is contained in the table stored in the storing unit 24. If the operation stage conforming to the retrieval key is found, the operating guide corresponding to the operation stage is acquired by referring to the table. The retrieving unit 23 outputs the acquired operating guide to the monitor 18. As a result, the operating guide corresponding to each operation stage is displayed on the display screen.

The operation of the guide controlling unit 20 will be explained with reference to FIGS. 4 and 5. FIG. 4 is a flowchart of an operation of masking a predetermined button or input field by the button switching unit 22. When the X-ray CT apparatus 1 starts and it is ready to operate by using the inputting unit 16, the guide controlling unit 20 is started at the same time. In the inputting device 16, the operating screen controlling unit 19 immediately displays the operating screen on the monitor 18.

In this state, the button switching unit 22 is waiting for input of a signal showing that the button to transfer to the guided mode has been pressed. As shown in FIG. 4A, when the operator of the apparatus presses the button of the guided mode overlaid and displayed on the operating screen (Yes, S101), the operation entering unit 17 having accepted the pressing operation inputs the signal corresponding to the pressing operation in the guide controlling unit 20. When the button switching unit 22 receives the inputted signal, it is determined that the button to transfer to the guided mode has been pressed.

When determining that the button to transfer to the guided mode has been pressed, the button switching unit 22 reads out the held mask image (S102), and overlays and displays in a predetermined position on the operating screen (S103). By overlay display of the mask image in the predetermined position, buttons and input fields of sub-functions other than the buttons and input fields necessary for promoting the scanning operation of the X-ray CT apparatus 1 are covered with the mask, and cannot be pressed by the operator of the apparatus.

Unless the button of the guided mode is pressed (No, S101), mask display is canceled, or non-display is maintained.

Figure 4B:
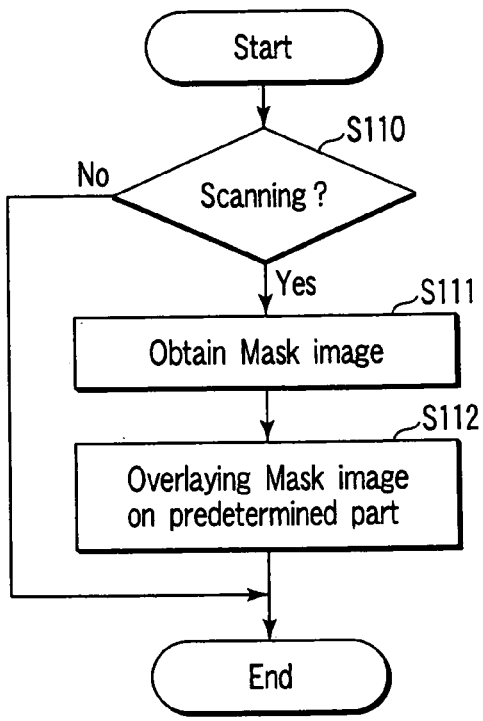
FIG. 4B is a flowchart explaining another operation of masking a predetermined position on the operating screen in the embodiment.
Figure 5:
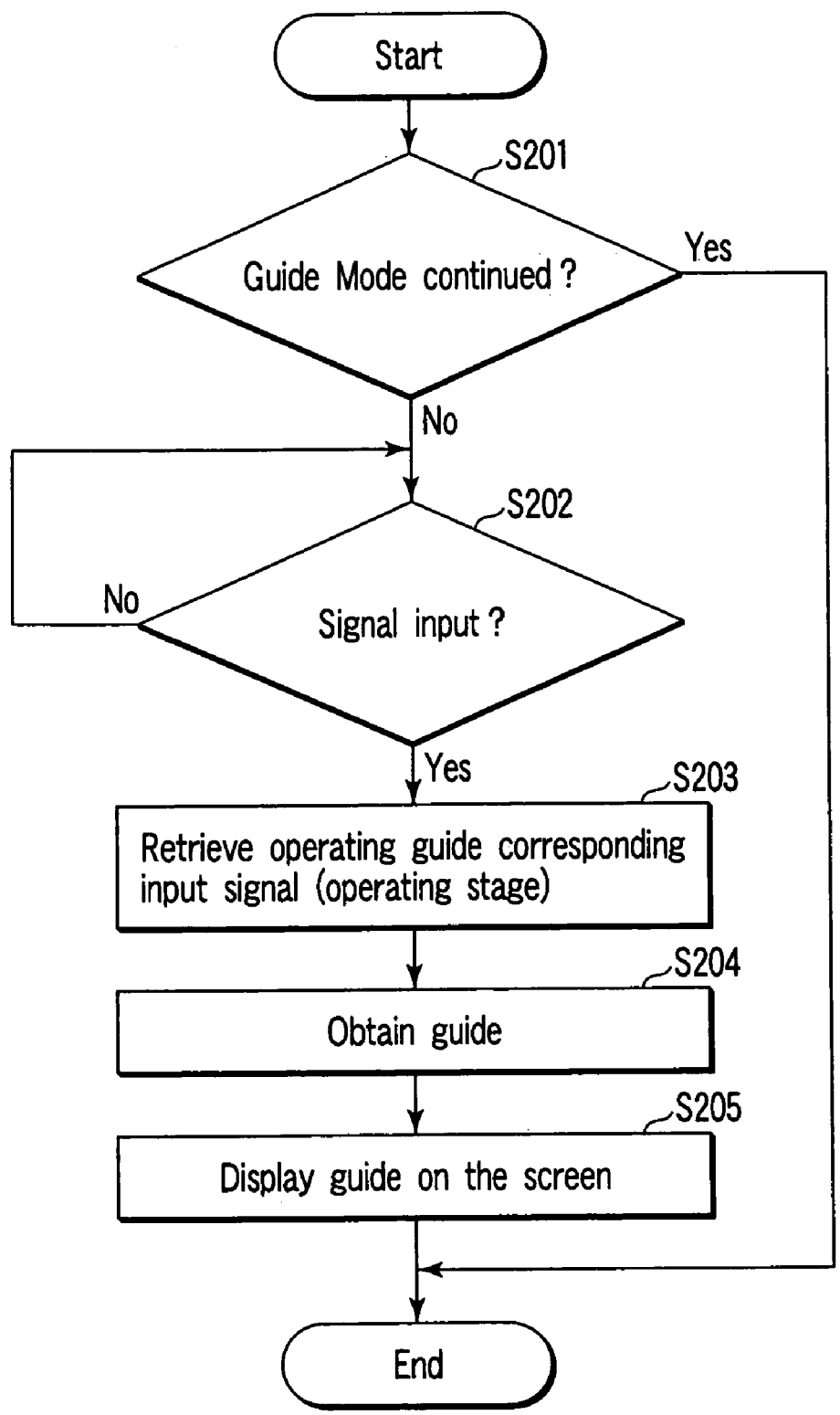
FIG. 5 is a flowchart explaining an operation of displaying an operating guide in the embodiment.

As shown in FIG. 4B, while transferring to the guided mode, when the operation completion signal of completion of transfer of the bed B or the like is inputted from the system controlling unit 11 to the guide controlling unit 20 (S110), that is, when transferred to the scan operation stage, the held mask image is read out (S111), and buttons and input fields not necessary in the scan operation are further masked on the operating screen (S112).

FIG. 5 is a flowchart of retrieving the operating guide and displaying the retrieved operating guide on the monitor 18 by means of the retrieving unit 23. The retrieving unit 23 also starts operation simultaneously with the X-ray CT apparatus 1 as part of the guide controlling unit 20. First, the operation entering unit 17 inputs the signal showing that the button to transfer to the guided mode has been pressed in the guide controlling unit 20, and if the cancel signal is not entered, that is, while the guided mode is active (Yes, S201), the retrieving unit 23 waits for input of the control signal, the operation completion signal at each operation stage, or the input waiting signal for the next operation stage from the system controlling unit 11, or the input signal from the operation entering unit 17 (S202).

When these signals are inputted (Yes, S02), the retrieving unit 23, using the inputted signals as retrieval keys, retrieves the table held in the storing unit 24, and retrieves the operating guides corresponding to the inputted signals (S203). The operating guide is image data for guiding an operating of the next operation stage, and the table shows the storing destination of the corresponding operating guide.

As a result of retrieval by the retrieving unit 23, when the corresponding operating guide is found, the operating guide is acquired from the shown storing destination (S204). When acquiring the operating guide, the retrieving unit 23 sends out the acquired operating guide to the monitor 18, and displays the operating guide on the display screen (S205).

While the X-ray CT apparatus 1 is in scanning operation (S206), the process returns to the step of determining whether or not the guided mode is active (S201). When the guided mode is active, the process goes to the step of waiting for signal input (S202), and the input waiting state continues.

By such a configuration and operation of the X-ray CT apparatus 1, operating guides and masks corresponding to the respective operation stages are displayed on the display screen. In FIGS. 6 to 16, operating guides and masks displayed at the respective operation stages will be explained below.

Figure 6A:
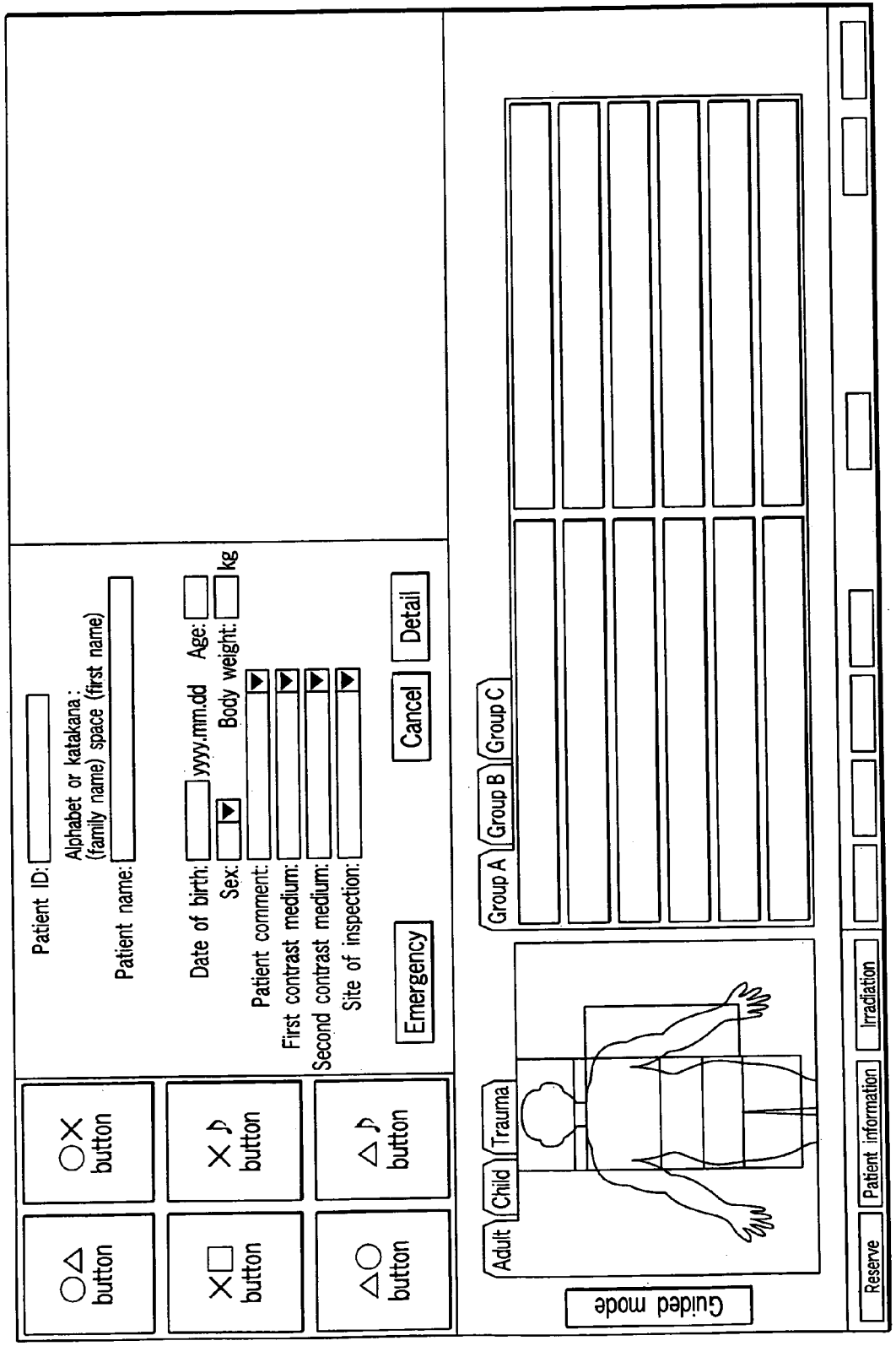
FIG. 6A is a view showing an operating screen at a scan preparatory stage in the embodiment.
Figure 6B:
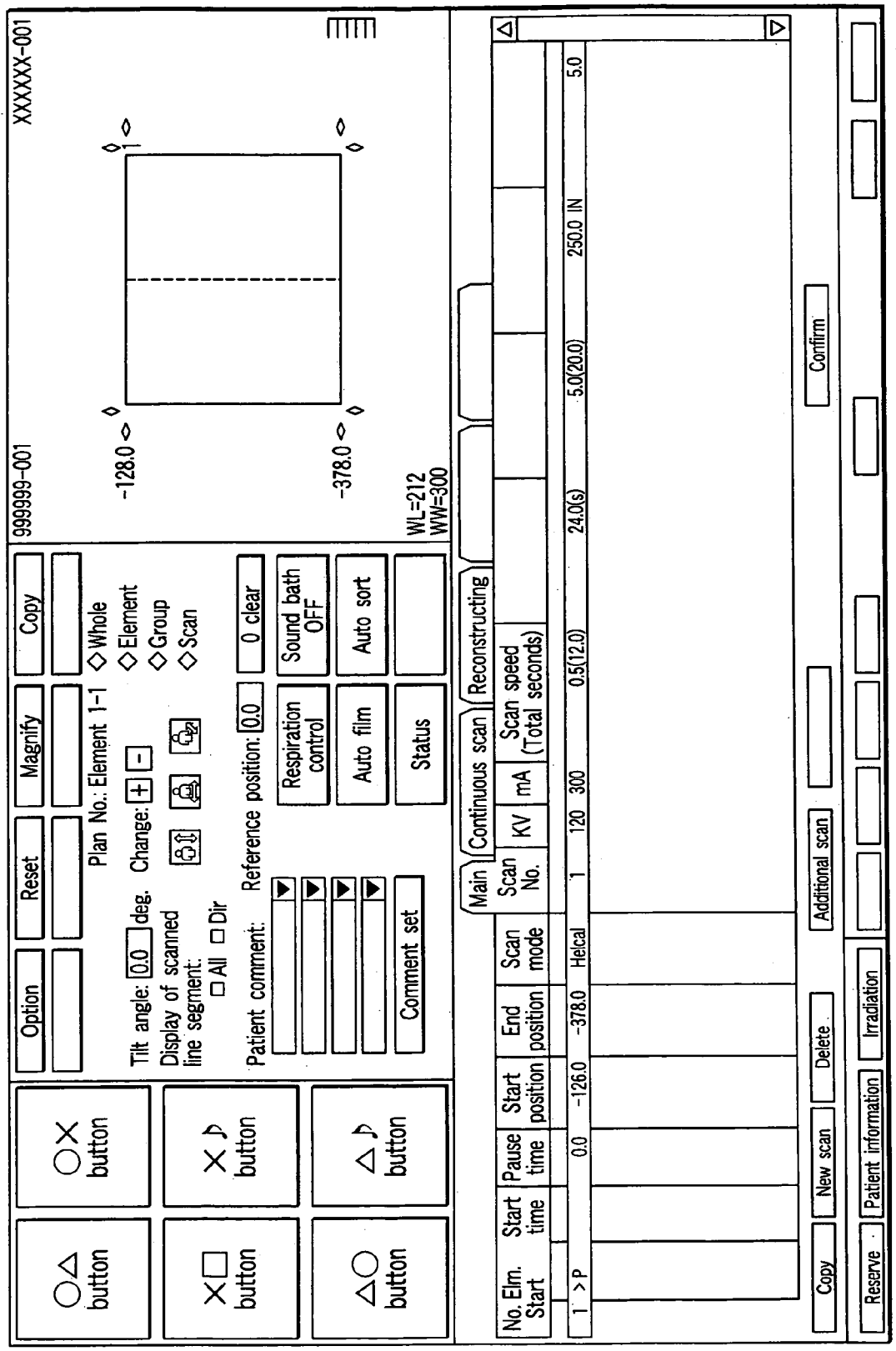
FIG. 6B is a view showing an operating screen at a scan planning stage in the embodiment.

The operating screen shown in FIG. 6A, FIG. 6B is displayed when the operating screen controlling unit 19 is in operation of starting the X-ray CT apparatus 1. The [Guided mode] button for transferring to the guided mode is displayed on the operating screen, and when pressing of this button is accepted in the operation entering unit 17, the guide unit is put in operation. On the operating screen, buttons and input fields for other operation stages, and the like are disposed.

Figure 7:
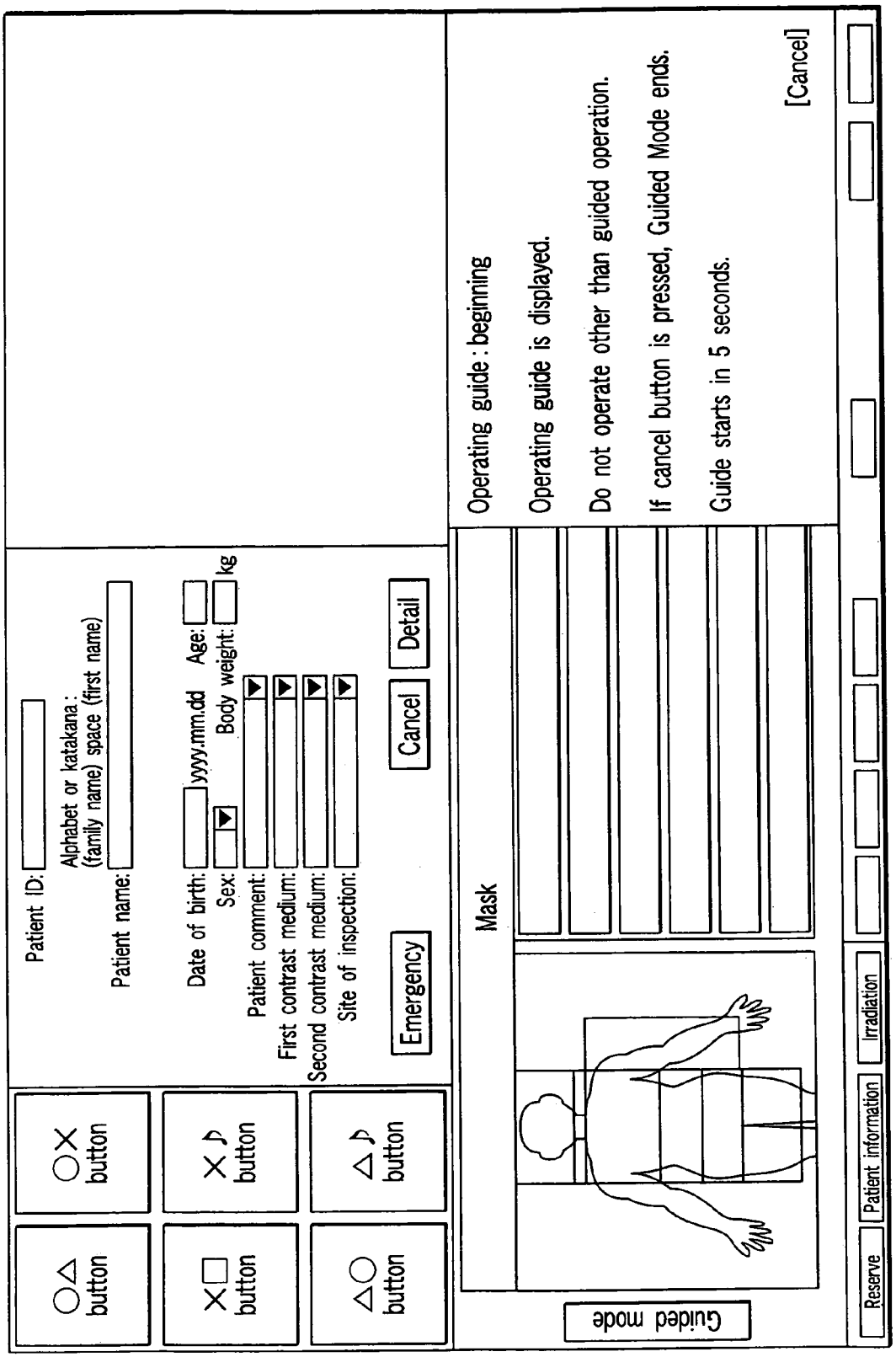
FIG. 7 is a view of a display screen showing an operating guide when transferring to a guided mode in the embodiment.

As shown in FIG. 7, when the [Guided mode] button is pressed on the operating screen, the guide controlling unit 20 is put in operation, and buttons and input fields not necessary for guiding a series of operations of the X-ray CT apparatus 1 are masked by means of the button switching unit 22. In the operating screen shown in FIG. 7, a scan tag for child, a scan tag for adult, and a scan tag for trauma out of the scan conditions are masked. When the operating entering unit inputs the signal showing that the [Guided mode] button has been pressed into the guide unit, the retrieving unit 23 retrieves the table by using this signal as a retrieval key, and displays image data of "Operating guide: beginning" on the display screen. The image data "Operating guide: beginning" informs that the scan operation of the X-ray CT apparatus 1 is transferred to the guided mode.

Figure 8:
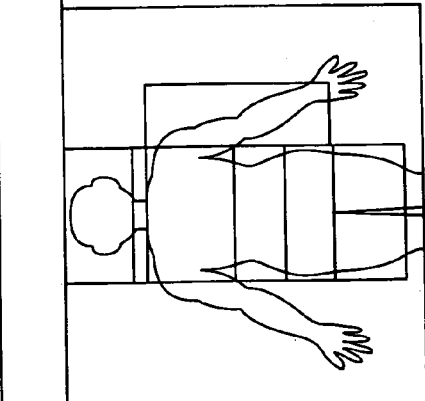
FIG. 8 is a view of a display screen showing an operating guide at a stage of subject ID and subject name storage in the embodiment.
Figure 11:
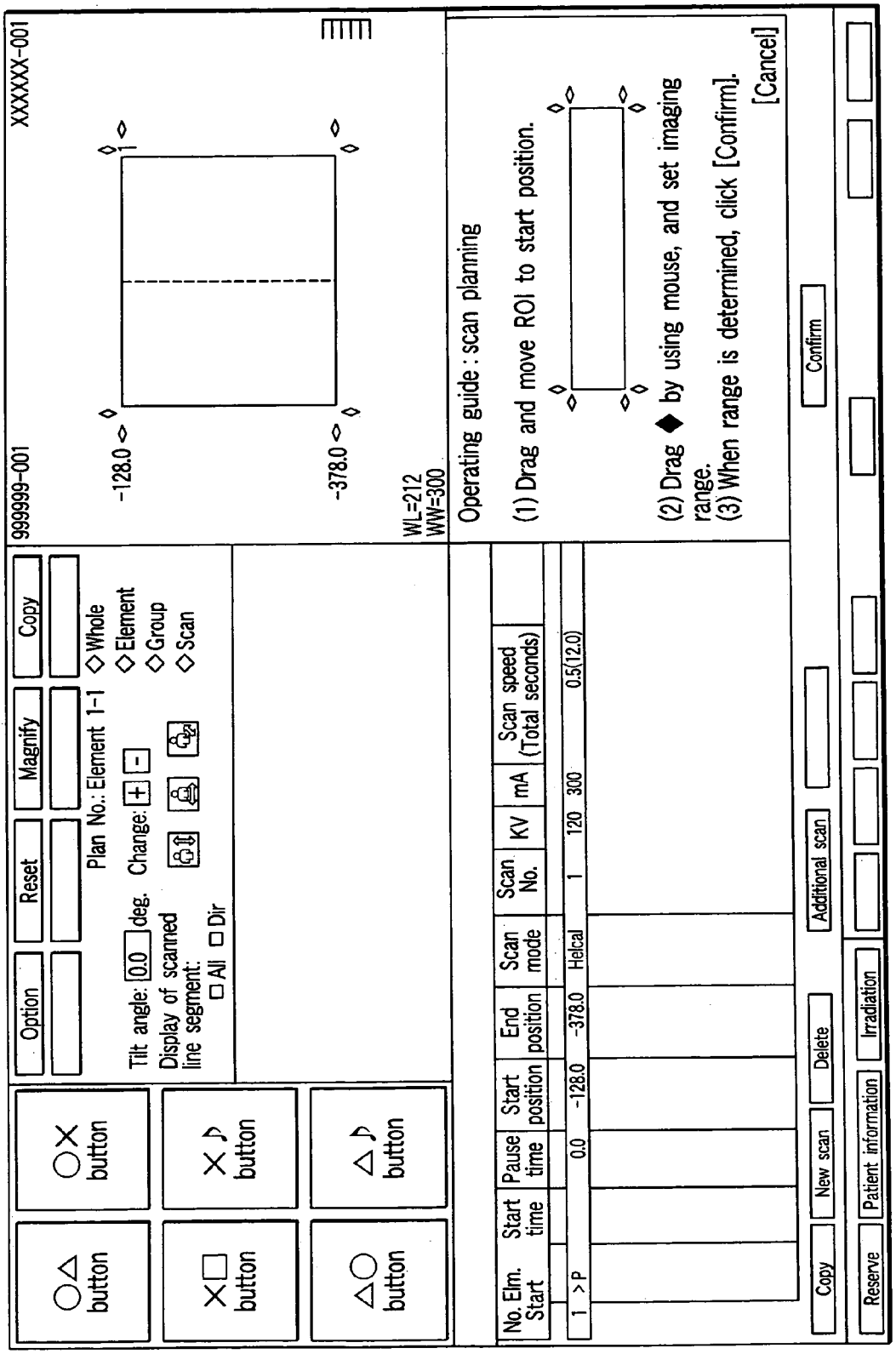
FIG. 11 is a view of a display screen showing an operating guide at a stage of scan planning operation in the embodiment.

In 5 seconds after displaying the operating guide of "Operating guide: beginning," the X-ray CT apparatus 1 transfers to the operation stage of storing the subject ID or subject name to be attached to the image to be scanned. As shown in FIG. 8, the retrieving unit retrieves "Operating guide: patient registration" and displays it on the monitor 18. The "Operating guide: patient registration" is a guide for urging input of the subject ID or subject name necessary at the operation stage of storing the subject ID or subject name.

When the subject ID or subject name is entered, and the system controlling unit 11 outputs to the guide controlling unit 20 the operation completion signal showing that the corresponding subject ID or subject name has been stored in the storing unit 14, the X-ray CT apparatus 1 transfer to the stage of scanogram scan operation. At this operation stage, as shown in FIG. 9, the button switching unit 22 masks the reference position setting button, respiration control button, sound batch OFF button, auto film button, auto sort button, status button, and patient comment input field which are disposed on the operating screen. When the operation completion signal showing completion of scan condition setting operation is outputted to the guide controlling unit 20, the retrieving unit retrieves the table by using this operation completion signal as a retrieval key, and displays the operating guide of "Operating guide: scanogram" on the display screen. The "Operating guide: scanogram" is a guide for urging input to scan scanogram of the subject.

When the operation completion signal informing of completion of scanogram operation is inputted in the system controlling unit 11, the X-ray CT apparatus 1 transfer to the operation stage of scan condition select. The retrieving unit 23 retrieves the table by using the operation completion signal showing that the subject ID or subject name has been stored as a retrieval key, and displays the operating guide of "Operating guide: scan condition select" shown in FIG. 10 on the display screen. The "Operating guide: scan condition select" is a guide for selecting the scanning position of the subject or selecting the scan condition.

When the scan condition is entered and the setting signal is inputted in the system controlling unit 11, the X-ray CT apparatus 1 transfers to scan planning operation. The inputting unit 16 receives the operation completion signal through the system controlling unit 11, and the retrieving unit 23 retrieves the table by using this signal as a retrieval key, and displays the operating guide of "Operating guide: scan planning" shown in FIG. 11 on the display screen. The "Operating guide: scan planning" is a guide for entering for scan planning operation, and in this embodiment, it is the guide for setting the scanning range.

Figure 12:
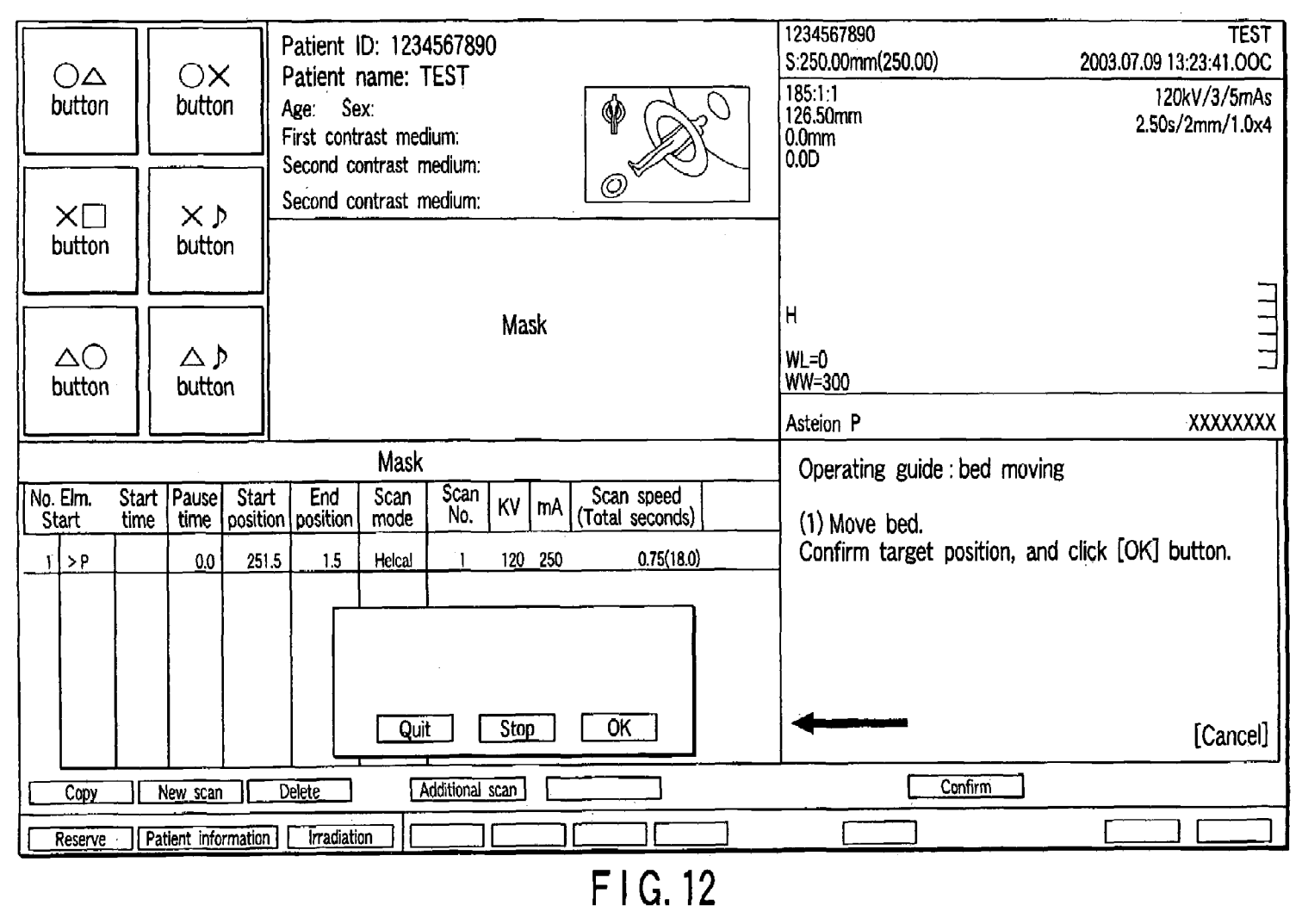

When the scanning range is inputted by using the operation entering unit 17, this input signal is received in the guide controlling unit 20, and the retrieving unit 23 retrieves the table by using this input signal as a retrieval key, and displays the operating guide of "Operating guide: bed move" shown in FIG. 12 on the display screen. The "Operating guide: bed move" is a guide for urging to input for moving the bed at the operation stage of moving the bed for scanning on the basis of the scan planning set at the scan planning operation stage.

When the operation completion signal showing completion of move of the bed is sent to the inputting unit and this signal is received in the guide controlling unit 20, the retrieving unit 23 refers to the table by using this signal as a retrieval key together with the input signal for selecting the scan mode preliminarily received from the inputting unit 16. In the scan mode selection, when a scan & scan mode, i.e., a scanning method for scanning in the first place, and then reconstructing is selected; or when a scan & view mode, i.e., a scanning method for scanning by repeating scanning, reconstructing, and image display is selected; or when a dynamic scan mode, i.e., a method for scanning the inside of the subject when a contrast medium flows into the predetermined position is selected, the display screen displays a corresponding operating guide of "Operating guide: S&S (scan & scan), S&V (scan & view), and dynamic scan" as shown in FIG. 13. The "Operating guide: S&S (scan & scan), S&V (scan & view), and dynamic scan" is a guide for urging input of scan start timing at the operation stage for scanning the inside of the subject according to any one of these scanning methods.

Figure 14:
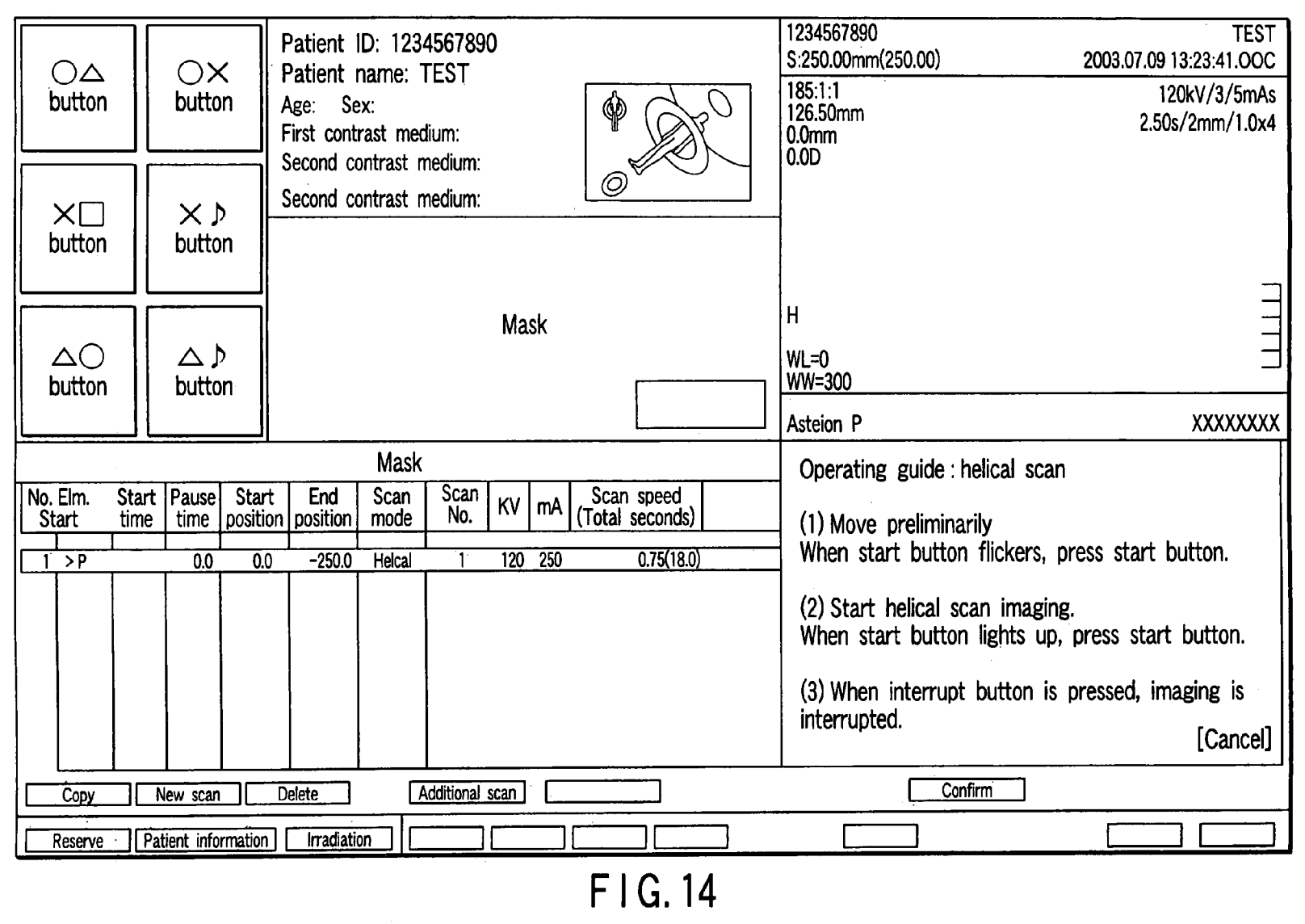

If, as the scan mode, a helical scan mode, i.e., a method for scanning the subject in a helical trajectory relatively is selected, the display screen shows the operating guide of "Operating guide: helical scan" shown in FIG. 14.

Figure 15:
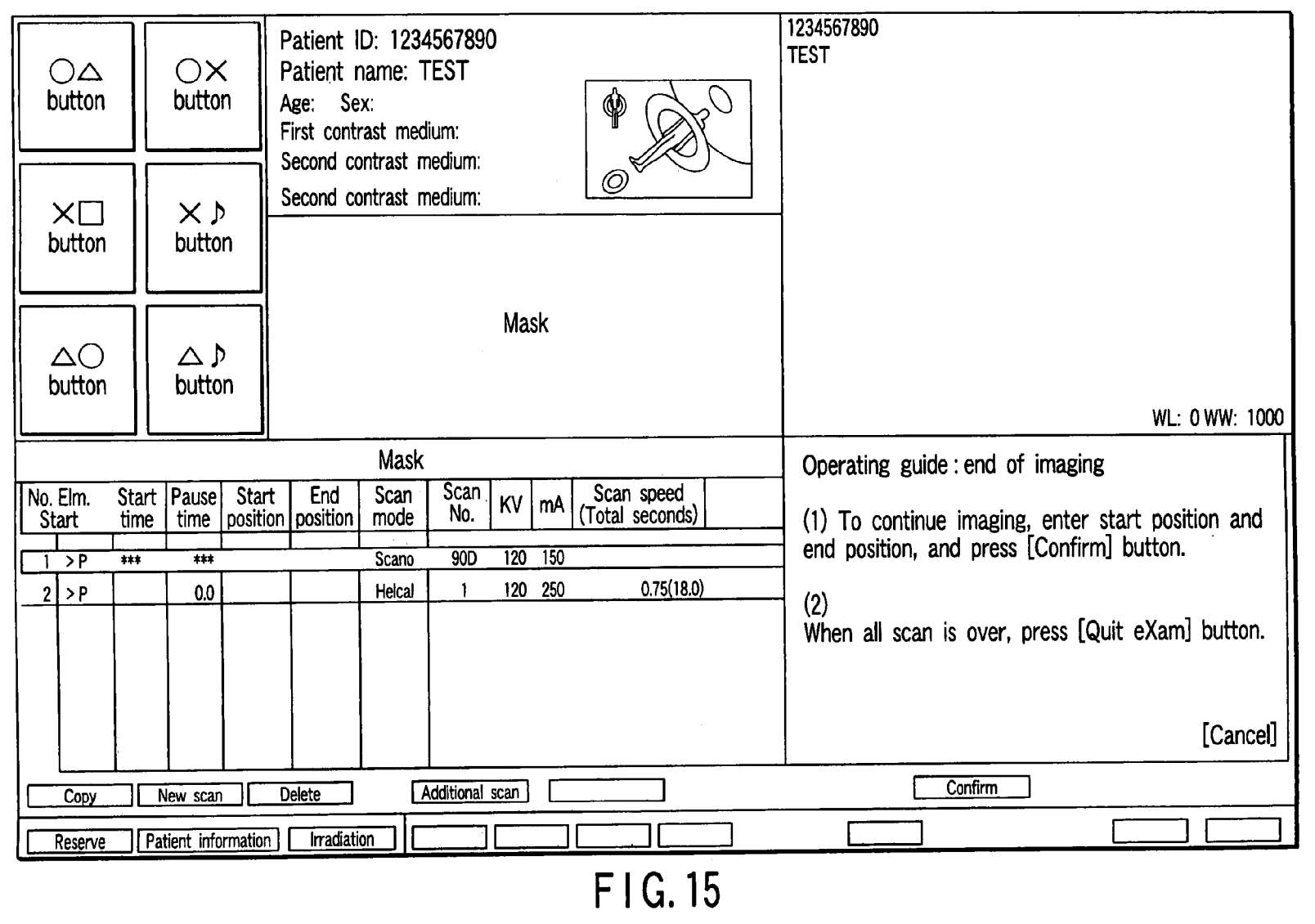

When the operation completion signal showing completion of scan operation is sent to the inputting unit 16, and this signal is received in the guide controlling unit 20, the retrieving unit 23 refers to the table by using this signal as a retrieval key, and displays the operating guide of "Operating guide: end of scan" shown in FIG. 15 on the display screen. The "Operating guide: end of scan" is a guide for urging to select the next operation stage, whether to continue scanning, or to end scanning and terminate the inspection operation.

Figure 16:
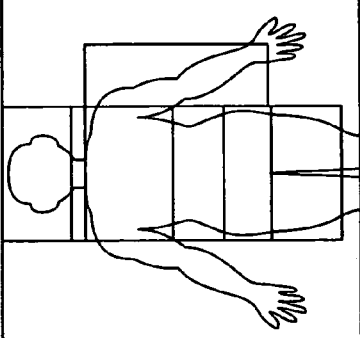
FIG. 16 is a view of a display screen showing an operating guide at a stage of inspection completion operation in the embodiment.

When the inspection completion operation is inputted from the inputting unit 16, the input signal is received in the guide controlling unit 20, the retrieving unit refers to the table by using this signal as a retrieval key, and displays the operating guide of "Operating guide: end of inspection" shown in FIG. 16 on the display screen. The "Operating guide: end of inspection" is a guide for urging to select the next operation stage, whether to repeat the scan in the same subject, or to move to scan of a next subject.

According to the invention, as described herein, the X-ray CT apparatus 1 stores operating guides corresponding to operations of the apparatus, acquires the operating guides corresponding to operation stages, and displays the acquired operating guides on the display screen. Therefore, even an operator of the apparatus not experienced enough in the X-ray CT apparatus 1 can handle easily without having any difficulty in operation at each operation stage, so that the inspection time can be shortened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
    a gantry including an X-ray tube and an X-ray detector in order to scan a subject;
    an operating guide unit configured to guide a series of operations at least necessary from preparation till completion of the scanning;
    a controlling unit configured to control the gantry in accordance with the operation; and
    a reconstructing unit configured to reconstruct image data on the basis of data collected by the scanning,
    wherein, in accordance with the operation stages, the operating guide unit selectively displays:
    a patient information input operating guide to urge input of a patient identification number and a patient name;
    a scanogram imaging operating guide to urge instruction of start of preliminary move of a bed for scanogram imaging, and instruction of start of scanogram imaging;
    a scan plan selection operating guide to urge selection of a scanning position and selection of a scan plan;
    a scan range setting operating guide to urge setting of a scan range on the scanogram;
    a bed move starting guide to urge instruction of start of move of the bed to the scan start position;
    a scan operating guide to urge instruction of start of the scan and to confirm scan interrupt operation; and
    a scan completion operating guide to confirm continuation of the scan and to urge instruction of completion of the scan;
    wherein the operating guide unit displays a guide concerning the operation, and does not display specific operation buttons on an operating screen.

2. The X-ray CT apparatus according to claim 1, further comprising a storing unit which stores data concerning the patient information input operating guide, data concerning the scanogram imaging operating guide, data concerning the scan plan selection operating guide, data concerning the scan range setting operating guide, data concerning the bed move starting guide, data concerning the scan operating guide, and data concerning the scan completion operating guide, in relation to respective corresponding operation stages.

3. The X-ray CT apparatus according to claim 2, wherein the data concerning the patient information input operating guide, data concerning the scanogram imaging operating guide, data concerning the scan plan selection operating guide, data concerning the scan range setting operating guide, data concerning the bed move starting guide, data concerning the scan operating guide, and data concerning the scan completion operating guide are image data individually.

4. The X-ray CT apparatus according to claim 3, wherein the scan operating guide includes instruction of start of preliminary move of the bed corresponding to helical scan.

5. The X-ray CT apparatus according to claim 3, wherein the scan plan selection operating guide includes a message for urging selection of the scanning position, a message urging selection of the scan plan, and a human figure model.

6. The X-ray CT apparatus according to claim 3, wherein the scan range setting operating guide includes a message for explaining move and expansion of a frame which expresses the scan range to be overlaid on the scanogram.

7. The X-ray CT apparatus according to claim 1, wherein the operating guide unit guides the operation when instruction of transfer to a guided mode is inputted.

8. The X-ray CT apparatus according to claim 1, wherein the specific operation buttons include at least one of:
    a button which specifies an operation of setting the scan start position to a set value;
    a button which specifies an operation of generating sound before and after scan depending on a scan time;
    a button which specifies an operation of setting sound for instructing respiration control or the like to an OFF state;
    a button which specifies an operation of filming images compiled by reconstructing;
    a button which specifies an operation of shuffling images compiled by reconstructing;
    a button which specifies an operation of acquiring a status of an electrocardiograph;
    a button which specifies an operation of storing comments; and
    a button which specifies an operation of setting scan conditions.

9. The X-ray CT apparatus according to claim 1, wherein the operating guide unit displays a guide concerning the operation, and limits specific functions.

10. The X-ray CT apparatus according to claim 9, wherein the operating guide unit displays interpretation concerning the limited functions.

11. An X-ray CT apparatus comprising:
    a gantry including an X-ray tube and an X-ray detector in order to scan a subject;
    an operating guide unit configured to guide a series of operations at least necessary from preparation till completion of the scanning;
    a controlling unit confianred to control the gantry in accordance with the operation; and
    a reconstructing unit configured to reconstruct image data on the basis of data collected by the scanning,
    wherein, in accordance with the operation stages, the operating guide unit selectively displays:
    a patient information input operating guide to urge input of a patient identification number and a patient name;
    a scanogram imaging operating guide to urge instruction of start of preliminary move of a bed for scanogram imaging, and instruction of start of scanogram imaging;
    a scan plan selection operating guide to urge selection of a scanning position and selection of a scan plan;
    a scan range setting operating guide to urge setting of a scan range on the scanogram;
    a bed move starting guide to urge instruction of start of move of the bed to the scan start position;
    a scan operating guide to urge instruction of start of the scan and to confirm scan interrupt operation; and
    a scan completion operating guide to confirm continuation of the scan and to urge instruction of completion of the scan, wherein the operating guide unit displays a guide concerning the operation, and does not accept operation of specific operation buttons on an operating screen.

12. An X-ray CT apparatus for reconstructing images of the inside of a subject, by performing an imaging operation including operation stages for executing scanogram imaging, various scans, and scan plans by means of emission of X-rays, the X-ray CT apparatus comprising:
   a displaying unit having a display screen;
   an operation entering unit which accepts an input at each operation stage;
   a storing unit which stores operating guides; and
   a guide controlling unit which acquires operating guides from the storing unit, and displays the acquired operating guides on the display screen to urge input by an operator,
   wherein the operating guide unit displays a guide concerning the operation, and does not display specific operation buttons on an operating screen.

13. The X-ray CT apparatus according to claim 12, wherein the storing unit stores a plurality of operating guides corresponding to respective operation stages, and
   the guide controlling unit acquires the operating guides corresponding to respective operation stages in accordance with the operation stages.

14. The X-ray CT apparatus according to claim 12, wherein the operation entering unit further accepts input to transfer to a guided mode, and
   the guide controlling unit acquires the operating guide only when the entering unit accepts the input to transfer to the guided mode.

15. The X-ray CT apparatus according to claim 12, wherein the operating guides include at least one of:

an operating guide corresponding to an operation stage of storing a subject ID or a subject name;

an operating guide corresponding to an operation stage of determining imaging conditions specialized for an operation of CT;

an operating guide corresponding to an operation stage of scanogram;

an operating guide corresponding to an operation stage of scanning by imaging first, and reconstructing later;

an operating guide corresponding to an operation stage of scanning by repeating imaging, reconstruction, and display of images of the inside of a subject;

an operating guide corresponding to an operation stage of dynamic scan;

an operating guide corresponding to an operation stage of helical scan; and an operating guide corresponding to an operation stage of scan planning.

16. An X-ray CT apparatus for reconstructing images of the inside of a subject, by transmitting X-rays through the subject, detecting the transmitted X-rays, and projecting reversely, the X-ray CT apparatus comprising:
   a displaying unit having a display screen;
   an operating screen controlling unit which displays an operating screen on the display screen; and
   a button switching unit which switches display and non-display of detail setting buttons out of buttons arranged on the operating screen.

* * * * *